United States Patent [19]
Kohn et al.

[11] Patent Number: 5,602,156
[45] Date of Patent: Feb. 11, 1997

[54] METHOD FOR INHIBITING METALLOPROTEINASE EXPRESSION

[75] Inventors: Elise C. Kohn, Olney; Lance A. Liotta, Potomac, both of Md.

[73] Assignee: The United States of America as represented by the Department of Health and Human Services, Washington, D.C.

[21] Appl. No.: 209,089

[22] Filed: Mar. 10, 1994

Related U.S. Application Data

[63] Continuation-in-part of Ser. No. 122,277, Sep. 17, 1993, abandoned.

[51] Int. Cl.$^6$ .................. A61K 31/41; A61K 31/415
[52] U.S. Cl. .................. 514/359; 514/255; 514/256; 514/258; 514/261; 514/383; 514/396; 514/398; 514/400
[58] Field of Search .................. 514/359, 396, 514/398, 400, 255, 256, 258, 261, 383

[56] References Cited

U.S. PATENT DOCUMENTS

| | | | |
|---|---|---|---|
| 4,590,201 | 5/1986 | Bochis et al. | 514/359 |
| 4,816,469 | 3/1989 | Bochis et al. | 514/359 |
| 4,847,257 | 7/1989 | Hupe et al. | 514/269 |
| 5,132,315 | 7/1992 | Kohn et al. | 514/359 |

FOREIGN PATENT DOCUMENTS

| | | |
|---|---|---|
| 0304221 | 2/1989 | European Pat. Off. |
| WO90/14009 | 11/1990 | WIPO |
| WO93/25536 | 12/1993 | WIPO |

OTHER PUBLICATIONS

Liotta, et al., *Nature*, 284:67–68 (1980).
Liotta, et al., *Biochemistry*, 20:100–104 (1981).
Stetler–Stevenson, et al., *J. Biol. Chem.*, 264:1353–1356 (1989).
Pozzatti, et al., *Science*, 23:223–227 (1986).
Collier, et al., *J. Biol. Chem.*, 263:6579–6587 (1988).
Brown, et al., *Cancer Research*, 50:6184–6191 (1990).
Castagna, et al., *J. Biol. Chem.*, 257:7847 (1982).
Berridge, et al., *Nature*, 341:197–205 (1989).
Aaronson, *Science*, 254:1146–1153 (1991).
Gusovsky, et al., *J. Biol. Chem.*, 268:7768–7772 (1993).
Tanaguchi, et al., *J. Biol. Chem.*, 268:2277–2279 (1993).
Chapron, et al., *Biochem. Biophys. Res. Comm.*, 158:527–533 (1989).
Kohn, et al., *J. Natl. Cancer Inst.*, 82:54–60 (1990).
Felder, et al., *J. Pharm. Exp. Therapeut.*, 257:967–971 (1991).
Kohn, et al., *Cancer Res.*, 52:3208–3212 (1992).
Hupe, et al., *J. Biol. Chem.*, 266:10136–10142 (1991).
Clark, et al., *Cell*, 65:1043–1051 (1991).
Merritt, et al., *J. Biol. Chem.*, 271:515–522 (1990).
Todaro, et al., *Proc. Natl. Acad. Sci. USA*, 77:5258–5262 (1980).
Templeton, et al., *Cancer Res.*, 50:5431–5437 (1990).
Fort, et al., *Nucleic Acids Res.*, 13:1431–1441 (1985).
Kohn, Elise C., "Development and Prevention of Metastasis," *Anticancer Research* 13:2553–2560 (1993).
Bochis, Richard J., et al. "Benzylated 1,2,3–Triazoles as Anticoccidiostats," *J. Med. Chem.* 34:2843–2852 (1991).
Kohn, E. C., et al., "Triazole derivatives, especially L 651582, for inhibition of tumor proliferation, invasion, and metastasis," *Chemical Abstracts* 115(23):85 (Sep. 1991).
Kohn, Elise, "Aging Issues in Invasion and Metastasis," *Cancer*, No. 2 Suppl., 71:552–557 (1993).
Hupe, Donald J., et al., "Anti–Proliferative Activity of L–651, 582 Correlates With Calcium–Mediated Regulation of Nucleotide Metabolism at Phosphoribosyl Pyrophosphate Synthetase," *J. Cell. Physiol.*, 144(3):457–466 (Sep. 1990).
Kohn, Elise C., et al., "Calcium Influx Modulates Expression of Matrix Metalloproteinase–2 (72–kDa Type IV Collagenase, Gelatinase A)," *J. Biol. Chem.* 269(34):21505–21511 (Aug. 1994).

*Primary Examiner*—Joseph McKane
*Attorney, Agent, or Firm*— Townsend and Townsend and Crew LLP

[57] ABSTRACT

Calcium homeostasis is an important regulator of MMP-2 transcription, activation and activity. Disclosed herein are compounds which inhibit the expression of matrix metalloproteinases in cells. Pharmaceutical application of these compounds to inhibit the expression of MMPs offers a new approach to cancer treatment as well as treatment for nerve healing, degenerative cartilagenous diseases, decubitus ulcers, arthritis, Alzheimer's disease, wound healing, proliferative retinopathy, proliferative renal diseases, corneal ulcers and fertility problems.

13 Claims, 7 Drawing Sheets

FIG. IC.    OVCAR3

METHOD FOR INHIBITING METALLOPROTEINASE EXPRESSION

The present application is a Continuation-In-Part of application Ser. No. 08/122,277, filed Sep. 17, 1993, now abandoned, the contents of which are incorporated herein by reference.

BACKGROUND OF THE INVENTION

The role of neutral metalloproteinases in the maintenance of normal body functions, such as bone remodeling and wound healing, requires tight regulation. This regulation is altered in malignancy where metalloproteinases are necessary for tumor neoangiogenesis and invasion.

One example of ectopic activity of an otherwise normal function is collagenolytic degradation of basement membrane and extracellular matrix by secreted matrix metalloproteinases (MMPs).

Proteolysis and interruption of the basement membrane requires activation of specialized matrix metalloproteinases which selectively degrade basement membrane collagens type IV and V, the type IV collagenases or gelatinases (MMPs). Liotta, et al., Nature 284:67–68 (1980). Two species of MMPs, the 72 kDa species (MMP-2, gelatinase A) and the 92 kDa species (MMP-9, gelatinase B) have been isolated, cloned and sequenced. Liotta, et al., ibid.; and Liotta, et al., Biochemistry 20:100–104 (1981). Both MMPs are secreted as latent proenzymes which require the removal of an 80 or 87 amino acid amino-terminal domain for activation. Stefler-Stevenson, et al., J. Biol Chem. 264:1353–1356 (1989). Little is known about the signaling pathways which mediate the production and activation of these enzymes. While the activity of these proteinases is metal ion ($Zn^{++}$)-dependent, the regulation of MMP production by divalent cations is unknown.

Recent studies have focused on the induction and activation of MMPs. Others have demonstrated that stable transfection of primary rat embryo fibroblast cells with activated Ha-ras resulted in the metastatic phenotype and increased production of type IV collagenases; this result was abrogated by simultaneous transfection of adenovirus E1A with Ha-ras (Pozzatti, et al., Science. 23:223–227 (1986)). Similar results were seen when Ha-ras was transfected into human bronchial epithelial cells (Collier, et al., J. Biol. Chem. 263:6579–6587 (1988)). Further investigation into the induction and subsequent regulation of MMP-2 demonstrated coordinate regulation of MMP-2 expression and function by treatment of human melanoma and fibrosarcoma cells with transforming factor-$\beta_1$(TGG-$\beta_1$), 12-O-tetradecanoylphorbol-13-acetate (TPA), interleukin-1 (IL-1), and retionic acid (RA). See, Brown, et al., Cancer Research 50:6184–6191 (1990). TGF-$\beta_1$ treatment resulted in induction of MMP-2 and inhibition of the interstitial collagenase, MMP-1. Conversely, TPA treatment produced inhibition of MMP-2 with induction of MMP-1. These results suggested involvement of transcriptional regulation and protein kinase C second messenger signaling pathways in the production of MMP-2. To date, there has been no demonstration of calciumdependent regulation of MMP-2 production or activation.

The action of the endogenous activator of protein kinase C, diacylglycerol, is mimicked by phorbol esters such as TPA (Castagna, et al., J. Biol. Chem. 257:7847 (1982)). Diacylglycerol is produced by hydrolysis of membrane phospholipids, such as phosphatidylinositol hisphosphate. Phosphatidylinositol hisphosphate is hydrolyzed to diacylglycerol and inositol trisphosphate by phospholipase C (PLC) -$\beta$ and -$\gamma$. These enzymes are regulated through different signal transduction pathways. PLC-$\beta$ is stimulated in response to ligand binding to seven transmembrane domain receptors which associate with guanine nucleotide binding protein intermediates (Berridge, et al., Nature 341:197–205 (1989)). In most instances, this activation is calcium-independent. Receptor tyrosine kinase stimulation by ligand binding may cause activation of PLC-$\gamma$ by specific tyrosine phosphorylation (Aaronson, Science 254:1146–1153 (1991)). This process may be dependent upon either calcium influx or intracellular calcium mobilization (Gusovsky, et al., J. Biol. Chem. 268:7768–7772 (1993); Tanaguchi, et al., J. Biol. Chem. 268:2277–2279 (1993); and Chapron, et al., Biochem. Biophs. Res. Comm. 158:527–533 (1989)). The activated phospholipases C then hydrolyze membrane phosphatidyl inositol bisphosphate to yield diacylglycerol and inositol polyphosphates, both which may act as second messengers. Diacylglycerol may be involved in vivo with activation of matrix metalloproteinases as suggested by the phorbol ester experiments or it may be the upstream activator of other signaling molecules such as mobilization of calcium.

Compound 1, shown below, is a novel calcium influx inhibitor with antiproliferative and antimetastatic activities (Kohn, et al., J. Natl. Cancer Inst. 82:54–60 (1990); Felder, et al., J. Pharm. Exp. Therapeut. 257:967–971 (1991); and Kohn, et al., Cancer Res. 52:3208–3212 (1992)). Investigation into the mechanism of action of compound 1 has demonstrated that it inhibits receptor-operated and voltage-gated calcium influx (Felder, et al., J. Pharm. Exp. Therapeut. 257:967–971 (1991); Hupe, et al., J. Biol. Chem. 266:10136–10142 (1991)), calcium-dependent arachidonic acid release (Felder, et al., J. Pharm. Exp. Therapeut. 257:967–971 (1991); Clark, et al., Cell. 65:1043–1051 (1991)) and tyrosine phosphorylation with activation of phospholipase C-$\gamma$ (Gusovsky, et al., J. Biol. Chem. 268:7768–7772 (1993)). These functions could also be inhibited by compound 2, shown below, a chemically different inhibitor of receptor operated calcium channels. See, Gusovsky, et al., J. Biol. Chem. 268:7768–7772 (1993); Merritt, et al., J. Biol. Chem 271:515–522 (1990). This confirmed the role of compound 1-mediated inhibition of calcium influx on these biochemical events. The ability of compound 1 to inhibit selected calcium-mediated signal transduction pathways made it an ideal tool with which to investigate the role of calcium regulation underlying the expression and activation of MMP-2.

1

SUMMARY OF THE INVENTION

It has now been discovered that calcium homeostasis is an important regulator of MMP-2 transcription, activation and activity, and that certain compounds inhibit the expression of matrix metalloproteinases in cells. This invention provides a method for using compound 1 and related compounds to inhibit the expression of MMPs in cells.

Pharmaceutical application directed to inhibiting the expression of MMPs offers a new approach to cancer treatment as well as treatment for nerve healing, degenerative cartilagenous diseases, decubitus ulcers, arthritis, Alzheimer's disease, wound healing, proliferative retinopathy, proliferative renal diseases, corneal ulcers and fertility problems.

BRIEF DESCRIPTION OF THE DRAWINGS

FIG. 1 shows several zymograms which illustrate the dose-dependent inhibition of MMP-2 gelatinase activity by compound 1 as well as the inhibition exhibited by several analogs of compound 1 as well as compound 2.

FIG. 2 shows the quantitation of compound 1 effects on MMP-2 gelatinase activity measured by laser densitometry of the zymograms in FIG. 1.

FIG. 3 shows a zymogram resulting from the addition of compound 1 to the zymogram activating medium and illustrates that compound 1 does not inhibit gelatinase activity of the metalloproteinases.

FIG. 4 is a Western immunoblot which confirms the dose-dependent of MMP-2 production in A2988 and HT1080 cells by compound 1.

FIG. 5 shows the effect on native and TGF-$\beta_1$ induced gelatinase activity of increasing exposure to compound 1.

FIG. 6 is a Western immunoblot of conditioned media from control, compound 1, and TGF-$\beta_1$ treated cells.

FIG. 7 is a Northern blot showing the effect of compound 1 on the expression of MMP-1 and MMP-2 in A2058 cells.

DESCRIPTION OF THE SPECIFIC EMBODIMENTS

The following abbreviations are used herein: MMP, matrix metalloproteinase; TGF-$\beta_1$, transforming growth factor-$\beta_1$; TIMP-2, tissue inhibitor of metalloproteinase-2; DMEM, Dulbecco's modified Eagle's medium; EDTA, ethylenediamine tetraacetic acid; EGTA, ethylenebis(oxyethylenenitrilo)tetraacetic acid; DMSO, dimethyl sulfoxide; GAPDH, glyceraldehyde-3-phosphate dehydrogenase.

As used herein, the term "alkyl" refers to a saturated hydrocarbon radical which may be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic group" refers to a group of unsaturated cyclic hydrocarbons containing one or more rings. The rings are typified by benzene which has a 6-carbon ring containing three double bonds. Groups containing multiple rings may have the rings fused together or linked covalently. Examples of such multiple ring aromatic groups are naphthyl, biphenyl and anthracenyl. The term "aromatic group" also refers to those groups described above which contain heteroatoms, for example, pyridyl and quinoxalyl. Other aromatic groups include certain 5-membered cyclic moieties such as the furan group and the thienyl group. Any of the aromatic groups described herein may be optionally substituted with halogen atoms, or other groups such as nitro, carboxyl, alkoxy and the like.

The term "alkoxyalkyl" refers to an alkoxy radical attached directly to an alkyl group. When used as a linking group, alkoxyalkyl refers to such radicals as —CH$_2$OCH$_2$—, —CH$_2$OCH$_2$CH$_2$—, —CH$_2$CH$_2$CH$_2$OCH$_2$—and —CH$_2$CH$_2$OCH$_2$CH$_2$—.

The term "substituted" refers to groups having additional moieties attached, such moieties including halogen atoms, and groups such as nitro, carboxyl, alkoxy, amino, carbamoyl and the like.

The term "effective amount" refers to an amount sufficient to elicit the desired biological response.

The present invention provides a method for inhibiting metalloproteinase expression in a cell using compounds of formula I.

$$Y-(CH_2)_p-Ar^1-X-Ar^2 \qquad (I)$$

The groups Ar$^1$ and Ar$^2$ are aromatic groups and may be the same or different. Examples of aromatic groups are phenyl, substituted phenyl, naphthyl, and substituted naphthyl.

The symbol X represents a linking group and may be O, S, SO$_2$, CO, CHCN, straight chain alkyl, alkoxy, and alkoxyalkyl.

The symbol Y represents a variety of structures. Some of these structures are represented by formula II:

in which A is N or CH; R$^1$ is hydrogen, —CONH$_2$ (carbamoyl), —CONHR$^5$, —CO$_2$H (carboxyl), —CO$_2$R$^5$, or —SO$_2$NH$_2$; R$^2$ is hydrogen, —NH$_2$ (amino), —NHCOC$_6$H$_5$ benzamido), —NHCOR$^5$, —NHCHO (formamido), —NHR$^5$ (alkylamino), or —N(R$^5$)$_2$ (dialkylamino) and R$^5$ is lower alkyl of from 1 to 6 carbon atoms. A preferred group for A is N. Preferred groups for R$^1$ are hydrogen, —CONH$_2$, —CONHR$^5$, and CO$_2$H. Particularly preferred are —CONH$_2$ and —CO$_2$H. Preferred groups for R$^2$ are —NH$_2$, —NHCOC$_6$H$_5$, —NHCOR$^5$, and —NHR$^5$. Particularly preferred groups for R$^2$ are —NH$_2$ and —NHCOR$^5$.

Other structures for Y are 1,2,4-triazolyl, pyrazinyl, purinyl, pyrimidinyl, 1,2,3-triazolo-{4,5-d}-pyrimidinyl, and their substituted analogs.

The symbol p represents an integer of from 0 to 4.

In certain preferred embodiments, this method uses a compound of formula I in which Y is a radical of formula II, A is N and $R^1$ is —$CONH_2$.

In further preferred embodiments, this method uses a compound of formula I in which Y is a radical of formula II, A is N, $R^1$ is —$CONH_2$, and $R^2$ is —$NH_2$.

In still further preferred embodiments, this method uses a compound of formula I in which p is an integer of from 0 to 2, $Ar^1$ and $Ar^2$ are both substituted phenyl, X is O, CO or CHCN, Y is a radical of formula II, A is N, $R^1$ is —$CONH_2$, and $R^2$ is —$NH_2$.

In the most preferred embodiment, this method uses a compound of formula I in which p is 1, $Ar^1$ is 2,6-dichlorophenyl, $Ar^2$ is 4-chlorophenyl, X is CO, Y is a radical of formula II, A is N, $R^1$ is —$CONH_2$, and $R^2$ is —$NH_2$.

In further embodiments, this invention provides a method for inhibiting the expression of MMP-2 in a cell.

In still further embodiments, this invention provides a method for inhibiting the expression of metalloproteinases in human cancer cells. Particularly preferred are the cell lines HT1080, OVCAR3 and A2058.

The compounds used in the present invention are either commercially available or may be prepared using conventional synthetic techniques. General synthetic routes to the novel compounds tested are provided below. Particular conditions are known to those of skill in the art. Table 1 below provides one group of compounds evaluated in developing the present invention.

TABLE 1

| Compound Number | A | $R^1$ | $R^2$ |
|---|---|---|---|
| 1 | N | carbamoyl | amino |
| 3 | N | carbamoyl | formamido |
| 4 | N | carbamoyl | acetamido |
| 5 | N | carbamoyl | benzamido |
| 6 | N | carboxyl | amino |
| 7 | CH | — | — |
| 8* | N | carbamoyl | amino |

*all Cl are replaced by H

Additionally, compounds 9–11, which are substructural analogs of those compounds in Table 1 were also evaluated in developing the present invention.

11

Compound 1 can be prepared by the method described in U.S. Pat. No. 4,590 201 Briefly, 2 6-dichloro-4-methylbenzoic acid is converted to its corresponding benzoyl chloride using thionyl chloride in dimethylformamide. Reaction of this benzoyl chloride with chlorbenzene in the presence of aluminum trichloride provides 4-(4-chlorobenzoyl)-3,5-dichlorotoluene. Bromination of the methyl group is carried out using N-bromosuccinimide in the presence of catalytic amounts of dibenzoyl peroxide to provide 4-(4-chlorobenzoyl)-3,5-dichlorobenzyl bromide. The benzyl bromide is then converted to the corresponding benzyl azide using potassium azide. Treatment of the 4(4-chlorobenzoyl)-3,5-dichlorobenzyl azide thus formed with 2-cyanoacetamide in the presence of sodium methoxide provides after workup, 5-amino-1-(4-(4-chlorobenzoyl)-3,5-dichlorobenzyl)- 1,2,3-triazole-4-carboxamide (Compound 1).

Compound 2 (shown in the Background of the Invention) can be prepared by the method described in Merritt, et al., *Biochem. J.,* 271:515–522 (1990). Briefly, 2-bromo-4'-methoxyacetophenone (Aldrich, Milwaukee, Wis., USA) is treated with imidazole to provide 1-(β-oxo-4-methoxyphenethyl)-1H-imidazole. Reduction of the ketone with sodium borohydride provides 1-(β-hydroxy-4-methoxyphenethyl)-1H-imidazole. Alkylation of the hydroxy moiety with the p-toluenesulfonate ester of 3-(4-methoxyphenyl)-1-propanol using potassium hydroxide in dimethylsulfoxide provide Compound 2 which is isolated as its hydrochloride salt.

Compounds 3–5 are prepared by treating compound 1 with the appropriate anhydride (formic acetic anhydride, acetic anhydride, or benzoic anhydride).

Compound 6 can be prepared by treating compound 1 with sufficient acid to hydrolyze the carboxamide to a carboxylic acid.

Compound 7 can be prepared by the reaction of 4-(4-chlorobenzoyl)-3,5-dichlorobenzyl bromide (used in the preparation of compound 1) with imidazole in the presence of base.

Compound 8 can be synthesized beginning with 4-methylbenzophenone. Treatment of 4-methylbenzophenone with N-bromosuccinimide provides 4bromomethylbenzophenone which is converted to its corresponding azide using sodium azide in ethanol. Treatment of the resultant azide with the anion of 2-cyanoacetamide provides compound 8.

Compounds 9 and 10 are commercially available (Aldrich, Milwaukee, Wis., USA)

Compound 11 can be synthesized beginning with 3-chlorobenzyl bromide. Conversion of the bromide to an azide can be accomplished using sodium azide in ethanol. Treatment of the resultant azide with the anion of 2-cyanoacetamide yields 11.

The compounds used in the present inventive method may be administered in any suitable manner, preferably with pharmaceutically acceptable carriers. One skilled in the art will appreciate that suitable methods of administering such compounds in the context of the present invention to an animal are available, and, although more than one route can be used to administer a particular compound, a particular route can often provide a more immediate and more effective reaction than another route. Pharmaceutically acceptable carriers are also well known to those who are skilled in the art. The optimal choice of carrier will be determined in part by the particular compound, as well as by the particular method used to administer the composition. Accordingly, there is a wide variety of suitable formulations of the pharmaceutical composition of the present invention.

Formulations suitable for oral administration can consist of (a) liquid solutions, such as an effective mount of the compound dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, mositening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiting only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight or surface area of the animal to be treated. The size of the dose also will be determined by the existence, nature, and extent of any adverse side-effects that might accompany the administration of a particular compound in a particular animal. In determining the effective amount of the active ingredient to be administered in the treatment or prophylaxis of cancer treatment, the physician needs to evaluate circulating plasma levels, toxicities, and tumor growth inhibition, and evidence of cancer progression.

In the practice of this invention, the compounds can be administered, for example, by intravenous infusion, orally, topically, intraperitoneally, intravesically or intrathecally for treatment of lymphomas, leukemias, and all solid tumors. The compounds could be applied in a suitable vehicle for the local and topical treatment of cancer. Tumors such as basal cell carcinoma and Kaposi's sarcoma could be treated by topical administration of the agents taught herein. Prevention of tumor recurrence by administration of the composition in a manner intended to reach the particular site where such cells are proliferating would be most advantageous. For example, intraperitoneal administration would be a means of treating tumors known to cause peritoneal carcinomatosis: Intravesical treatment of transitional cell carcinoma and topical treatment of mycosis fungoides are further examples of site-directed treatment. Systemic administration may be accomplished by continuous infusion, bolus parenteral treatment, or release from an implanted slow release depot. It is obvious that this method can supplement treatment of cancer by any conventional therapy including cytotoxic agents and biologic response modifiers. The method disclosed may be used in any malignancy as a means of treatment to prevent the transition from in situ to invasive carcinoma or invasive to metastatic carcinoma.

For oral administration, compounds of the present inventive method can be administered at the rate up to 3000 mg/m$^2$ body surface area, which approximates 6 grams/day in the average patient. This can be accomplished via single or divided doses. For intravenous administration, such compounds can be administered at the rate of up to about 2500 mg/m$^2$/d. For intravesicle administration, such compounds can be administered at the rate of up to about 2500 mg/m$^2$/d. For topical administration, the rate can be up to about 2500 mg/m$^2$/d. The dose for inhalation/aerosol administration can be up to about 2500 mg/m$^2$/d. Direct intraperitoneal administration can be performed using up to about 3000 mg/m$^2$/d. The dose for reservoir administration to the brain or spinal fluid can be up to about 2000 mg/m$^2$/d. For slow release intraperitoneal or subcutaneous administration, the dose can be up to about 10 g/day in a bolus. For intrathecal administration, the dose can be up to about 2000 mg/m$^2$/d.

The methods taught herein are not restricted to use in treatment of malignancies. Disease conditions such as endometriosis, psoriasis, and eczema which result from localized spread of diseased cells may also be advantageously treated. Additionally, disease states which rely on calcium-mediated signal transduction/proliferation may also be treated. Such diseases include the collagen vasculitides (i.e., systemic lupus erthythematosis and rheumatoid arthritis), neurologic diseases (i.e., dementia and nerve conduction diseases), diseases of transport (i.e., cystic fibrosis), diseases of proliferation (i.e., diabetic retinopathy, glomerulopathies), toxic effects of agents (i.e., cisplatinrelated neuropathy), and cellular dysfunction (i.e., myelodysfunction syndromes).

The following examples illustrate the in vitro assays and results used to evaluate the efficacy of the compounds of this invention.

EXAMPLES

Materials

Compound 1 was supplied as a powder by the Developmental Therapeutics Program of the National Cancer Institute (Bethesda, Md., USA). A 20 mM stock solution was made in DMSO or PEG-400, and aliquots were stored at −70° C. For use, a 10 μM solution was prepared daily in media (DMEM), and serial dilutions were made as needed. Compound 2 was purchased from Biomol (Plymouth Meeting, Pa., USA), and maintained in the same fashion as compound 1.

Other reagents were either reagent grade or HPLC grade from commercial sources (Sigma Chemical Co., St. Louis, Mo., USA and Aldrich, Milwaukee, Wis., USA).

The HT1080 and OVCAR3 cell lines were obtained from the American Type Culture Collection, (Rockville, Md., USA)

A2058 was derived from a brain metastasis of a patient with melanoma (see, Todaro, et al., *Proc. Natl. Acad. Sci. USA*, 77:5258–5262 (1980));

Cells were cultured in DMEM or RPMI with 10% fetal calf serum unless otherwise stated and were used for no more than 10 passages from thaw.

Conditioned media for zymogram and Western blot analysis were produced under serum-free conditions. Cells (2 million) were plated in 25 cm$^2$ flasks in serum-containing medium and cultured overnight. Serum-containing medium was removed and the cell monolayers were washed twice with DMEM/ITS (DMEM containing insulin (5 μg/mL), transferrin (5 μg/mL), and selenium (5 ng/mL)). The resultant cells were fed with 3 mL of DMEM/ITS and additives as described in the Examples for two 24 hour periods. Conditioned media samples were collected at 24 hours and cells were refed with fresh DMEM/ITS containing the described additives for an additional 24 hours. Conditioned media samples were centrifuged to remove cells and debris then frozen at −20° C. until use. Freeze and thaw cycles of the conditioned media were limited to no more than two.

Precast gelatin polyacrylamide gels and 4–20% polyacrylamide gradient gels were from Novex (San Diego, Calif., USA). Immunoblot color development reagents were from Bio-Rad Laboratories, Inc. (Hercules, Calif., USA). BCA protein assay materials were purchased from Pierce Chemical Co. (Rockford, Ill., USA). Transforming growth factor-$\beta_1$ (TGF-$\beta_1$) was purchased from R&D (Minneapolis, Minn., USA). Molecular reagents were from New England Nuclear (Boston, Mass., USA) and Gibco BRL (Rockville, Md., USA).

EXAMPLE 1

Inhibition of Gelatinase Activity of Human Cancer Cell Lines

This example describes the effect of compound 1 and structural analogs on gelatinase activity of three different human cancer cell lines using gelatin zymography. Quantitation of the effect was evaluated by laser densitometry of the resultant zymograms.

A2058 human melanoma cells, human HT1080 fibrosarcoma cells, and OVCAR3 human ovarian cancer cells were incubated with increasing concentrations of compound 1 (0.2–20 μM) or DMSO control (0.05%) and subjected to gelatin zymography. Aliquots of conditioned medium (15 μL) were electrophoresed on gelatin-containing 10% PAGE gels under nonreducing but denaturing conditions. These conditions allow the different gelatin-degrading species (MMPs) to separate by size. The enzymes renature after removal of the SDS by incubation of the gel with 2.5 % Triton X-100, and degrade the gelatin substrate present in the polyacrylamide gel upon overnight incubation in low salt collagenase buffer. Bands of clearing, seen after Coomassie blue staining correspond to areas of gelatinase activity.

OVCAR3 conditioned media samples were concentrated 10-fold prior to zymography.

Figure 1A:
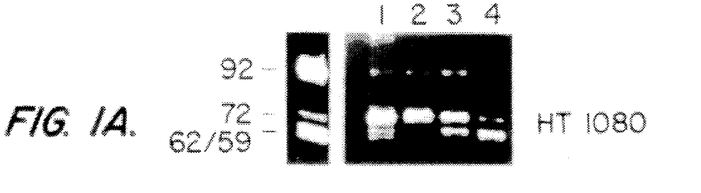
Figure 1B:
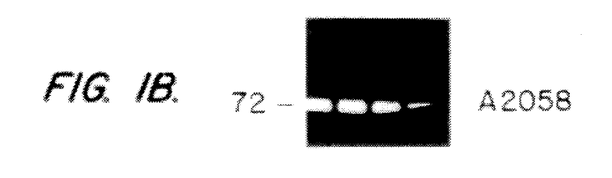
Figure 1C:
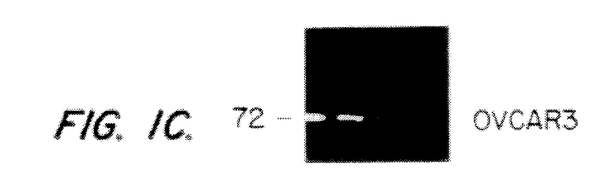

Known concentrated conditioned medium from HT1080 cells was used for identification of the gelatinase species as marked in FIG. 1A: 92 kDa, gelatinase B/MMP-9; 72 kDa, gelatinase A/MMP-2 latent form; 65 kDa intermediate and 62 kDa activated forms of MMP-2. The activated form of MMP-2 results from cleavage of the amino terminal domain.

FIG. 1 shows the results from HT1080 cells (1A), A2058 cells (1B) and OVCAR3 cells (1C). Lane 1 corresponds to cells treated only with 0.05% DMSO as a control. Lanes 2–4 correspond to cells treated with 0.2, 2.0 and 20 μM compound 1, respectively.

Figure 2A:
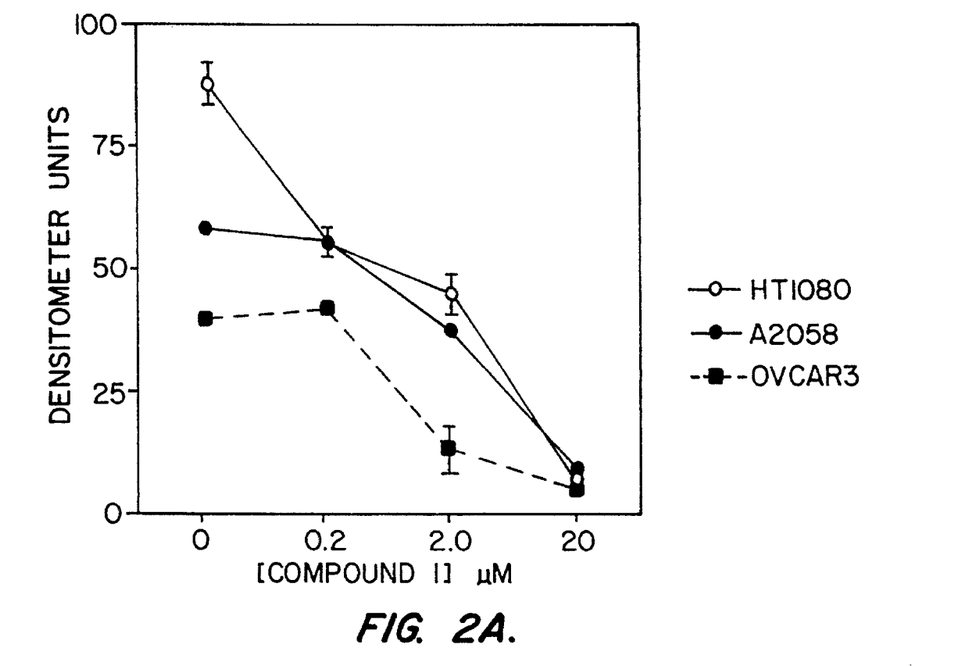
Figure 2B:
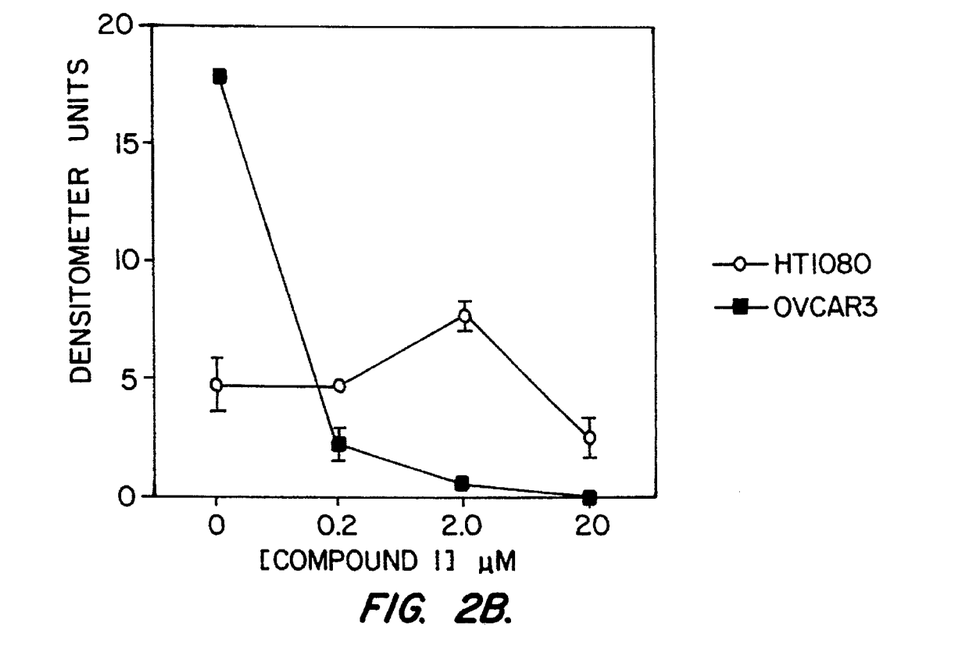

Treatment of the three different human cancer cell lines with compound 1 resulted in a dose dependent reduction of MMP activity. A shift to activated species with subsequent decrease in total activity was seen for the HT1080 cell line. Quantitation of the zymograms in FIGS. 1A–1C were carded out using laser densitometry. The results were normalized to DMSO control lanes and are presented in FIG. 2. A greater than 80% reduction in activity of all MMP-2 species was seen for all cell lines. Treatment with 20 μM compound 1 caused an almost complete reduction of activated MMP-2 in the A2058 and OVCAR3 cell lines, but only a 75 % reduction of the HT1080 line.

Figure 1D:
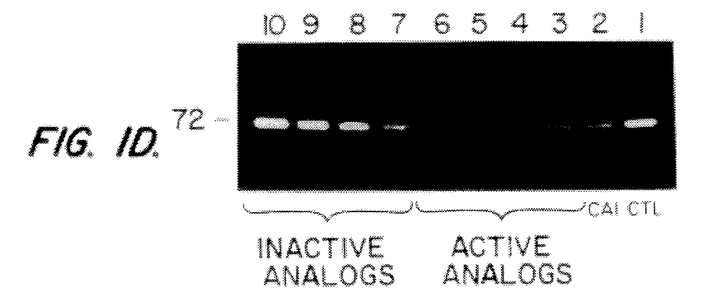

The effect of structural analogs on the gelatinase activity of A2058 cells was similarly evaluated. FIG. 1D shows the zymogram which resulted from incubation of conditioned media from A2058 cells with DMSO control (lane 1), compound 1 10 μM (lane 2), and 10 μM concentrations of compounds 3–6 and 8–11 (lanes 3–10, respectively). Compounds 3–6, which have been shown to inhibit activity in signal transduction and proliferation assays (see U.S. patent application Ser. No. 07/985,402 and Kohn, et al., *Cancer Research* in press) also reduced gelatinolytic activity. Compounds 8–11 which do not inhibit calcium influx, arachidonic acid release, or proliferation (see U.S. patent application Ser. No. 07/985,402), also did not reduce gelatinolytic activity.

Figure 1E:
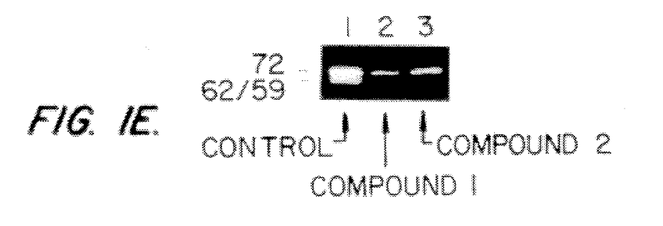

Treatment of A2058 cells with compound 2 provided further correlation of calcium regulation with MMP-2 activity. Compound 2 is structurally dissimilar to compound 1 but is an effective inhibitor of receptor-operated calcium channels with reactivity against some voltage-gated calcium channels. It has been shown to have identical effects as compound 1 in receptor-operated calcium influx. See, Gusovsky, et al., *J. Biol. Chem.* 268:7768–7772 (1993). FIG. 1E shows a zymogram resulting from the treatment of A2058 cells with 0.05 % DMSO (control, lane 1), 10 μM compound 1 (lane 2) and 10 μM compound 2 (lane 3). Both compound 1 and compound 2 reduced MMP-2 activity.

EXAMPLE 2

Type of Inhibition of Gelatinolytic Activity by Compound 1

This experiment was carded out to determine if the compound 1-induced reduction of gelatinolytic activity was direct (action at the enzyme or by chelation of Ca$^{++}$) or occuring at the level of enzyme production. Compound 1 has been shown to inhibit receptor-stimulated and voltage-gated calcium entry across cell membranes without evidence for chelation of calcium by compound 1. See, Felder, et al., J. Pharm. Exp. Therapeut. 257:967–971 (1991) and unpublished observations by the inventors.

Figure 3A:
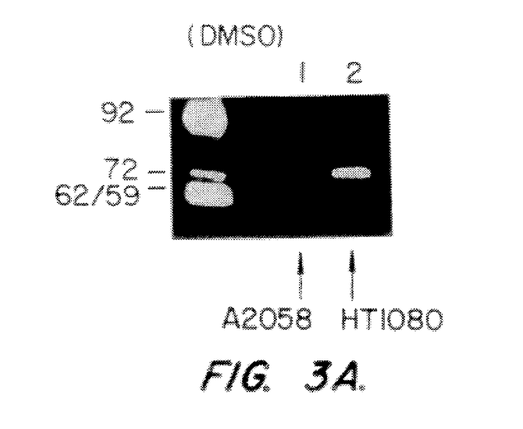
Figure 3B:
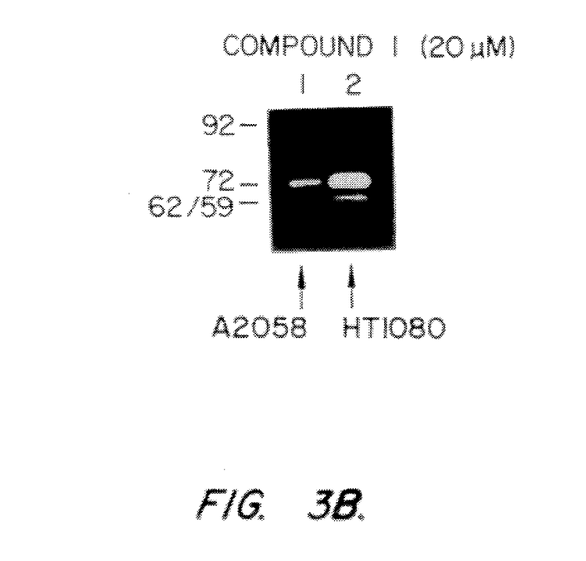

Gelatin zymography was carded out using control conditioned media from A2058 cells and HT1080 cells in the absence of compound 1. Zymogram slices were incubated in low salt collagenase buffer with control (DMSO 0.1%), an inhibitory dose of compound 1 (20 µM), or the calcium chelators EGTA (10 mM) and EDTA (10 mM). Inclusion of EDTA in the incubation buffer has been shown by others to inhibit gelatinolytic activity. See, Brown, et al., *Cancer Res.* 50:6184–6191 (1990). FIG. 3 shows the control (A) and compound 1-treated (B) portions of the zymogram along with known concentrated conditioned medium from HT1080 cells which was used for identification of the gelatinase species (as in Example 1). Lane 1 for each of the zymograms corresponds to A2058 while lane 2 corresponds to HT1080. Incubation of the enzymes with compound 1 at concentrations which reduce MMP-2 activity from cell-derived conditioned media did not effect its activity in isolation. The results with EGTA and EDTA (not shown) confirmed the requirement for metal ion ($Ca^{++}$) in the activation buffer and further confirmed that the mechanism of action of compound 1 reduction is not due to calcium chelation.

The lack of reduction of gelatinolytic activity in conditioned medium by compound 1 suggested that the effect of compound 1 on MMP-2 occured biochemically at the level of enzyme production or above.

EXAMPLE 3

Effect of Compound 1 on the Presence of MMP-2 and Its Activated Species

This example illustrates the dose-dependent effects of compound 1 on the presence of MMP-2 and its activated species. Western immunoblots were used to detect the effect of compound 1 on the presence of MMP-2 and its activated species and for crude quantitation of MMP-2 presence.

A2058 and HT1080 conditioned media samples were concentrated 10-fold using ultrafiltration units excluding material of less than 10 or 30 kDa in molecular weight. Aliquots of 15 µL were electrophoresed on 4–20% gradient PAGE gels, electrically transferred to membranes and immunoblotted with specific polyclonal antibody to proMMP-2. This antibody, made to the MMP-2/TIMP-2 complex recognizes the latent and activated MMP-2 species and crossreacts with TIMP-2 (21 kDa).

Figure 4A:
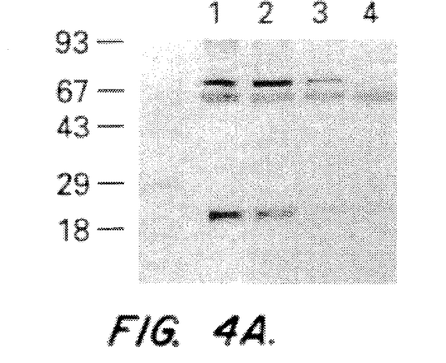
Figure 4B:
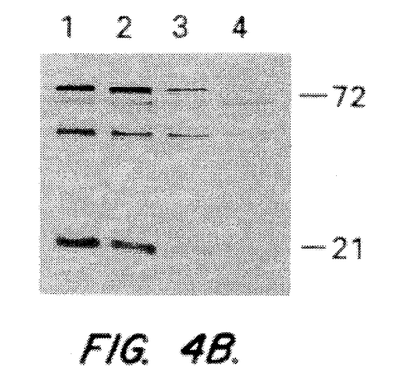
Figure 4C:
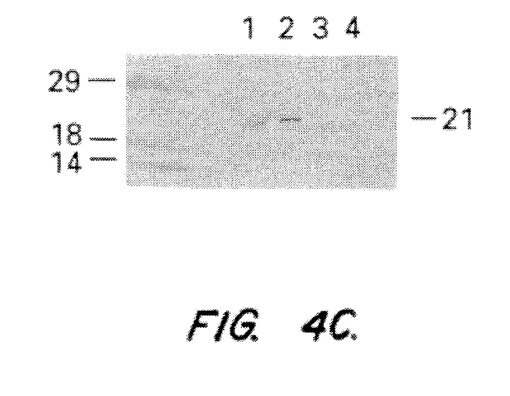

Compound 1 caused a dose-dependent reduction of the presence of the MMP-2 species (FIG. 4). This reduction included a shift to the lower molecular weight activated species before more complete reduction of all species was seen after incubation with 20 µM compound 1. This data suggests that compound 1 may have a selective effect on the production of MMP-2 by the tumor cells.

EXAMPLE 4

Effect of Compound 1 and TGF-$\beta_1$ on Gelatinase Activity and Presence of MMPS TGF-$\beta_1$ has been shown to stimulate production of MMP-2 by stimulation of RNA expression. The effect of compound 1 on TGF-$\beta_1$-stimulated MMP-2 production was evaluated in A2058 and HT1080 cell lines.

A2058 and HT1080 cells were incubated with compound 1 (2 µM), with or without TGF-$\beta_1$(5 ng/mL) for 24 and 48 hours prior to harvest of conditioned media. Aliquots were subjected to gelatin zymography as described in Example 1.

Figure 5A:
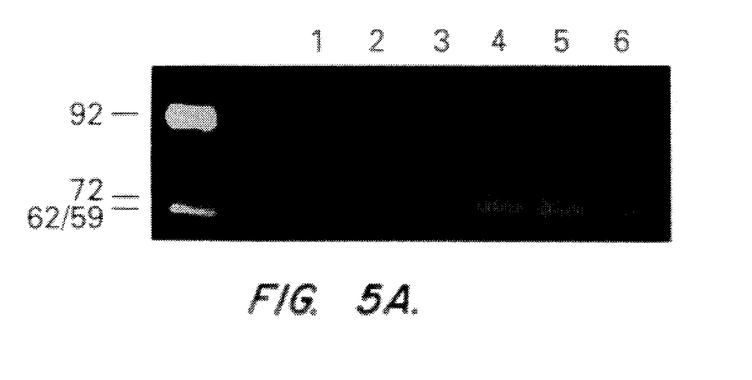
Figure 5B:
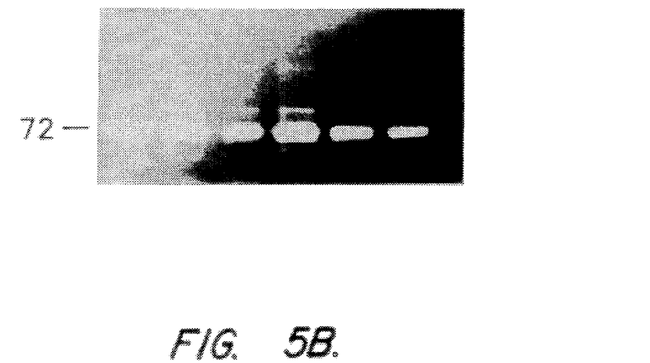

Known concentrated conditioned medium from HT1080 cells was used for identification of the gelatinase species (92 kDa, gelatinase B/MMP-9; 72 kDa, gelatinase A/MMP-2 latent form; 65 kDa intermediate and 62 kDa activated forms of MMP-2). FIG. 5 shows the results of these treatments for A2058 (5A) and HT1080 (5B).

Lane 1 is the control resulting from treatment of the cells with 0.1% DMSO. Lanes 2 and 3 correspond to those cells which are treated with 2 µM compound 1 in the absence of TGF-$\beta_1$ for 24 and 48 hours, respectively. Lane 4 corresponds to cells which have been treated with TGF-$\beta_1$ in the absence of compound 1. Lane 5 corresponds to cells which have been treated with TGF-$\beta_1$ for 48 hours with compound 1 being added to the incubation mixture for the final 24 hours. Lane 6 corresponds to cells which have been treated for 48 hours with both TGF-$\beta_1$ and compound 1.

Compound 1 reduction of gelatinase activity increased from 24 to 48 hr exposure (FIG. 5, lanes 1–3). TGF-$\beta_1$ increased gelatinase activity when used alone for 48 hr (lane 4). This increase was inhibited by co-incubation for 48 hr with compound 1 (lane 6). However, 48 hr exposure of the cells to TGF-$\beta_1$ with addition of compound 1 over the final 24 hr showed little effect due to compound 1. These results suggest that compound 1 must be present during induction of MMP-2 transcription by TGF-$\beta_1$ (first 24 hours) for compound 1 to inhibit the effects of TGF-$\beta_1$ and suggest that compound 1 also may have an effect on MMP-2 transcription. Table 2 provides a densitometric analysis of the effect of compound 1 and TGF-$\beta_1$ on Type IV collagenase species.

TABLE 2

Densitometric Analysis of the Effect of Compound 1 and TGF-$\beta_1$ on Type IV collagenase species

| A. A2058 MMP-2 species. | | | | |
|---|---|---|---|---|
| | 72 kDa | | 65 + 62 kDa | |
| | TGF-$\beta_1$ | | TGF-$\beta_1$ | |
| Exposure (hr) to Compound 1 (2 µM) | − | + | − | + |
| 0 | 100* | 68 | 100 | 0 |
| 24 | 84 | 44 | 14 | 0 |
| 48 | 45 | 36 | 0 | 0 |

| B. HT1080 MMP-2 and MMP-9 species. | | | | | | |
|---|---|---|---|---|---|---|
| Exposure (hr) to Compound 1 | 92 kDa TGF-$\beta$ | | 72 kDa TGF-$\beta$ | | 65 + 62 kDa TGF-$\beta$ | |
| (2 µM) | − | + | − | + | − | + |
| 0 | 100 | 64 | 100 | 47 | 100 | 192 |
| 24 | 73 | 78 | 10 | 52 | 125 | 194 |
| 48 | 12 | 14 | 0.6 | 10 | 24 | 116 |

*The control band was defined as 100% gelatinase activity and the other bands were normalized to it. Numbers reflect triplicate measurements from each zymogram band of representative zymograms. Standard deviations, not shown, were ≦10%.

Figure 6A:
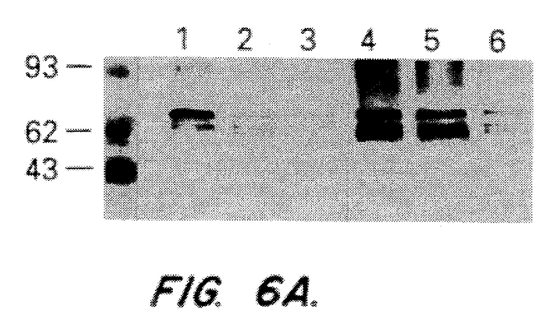
Figure 6B:
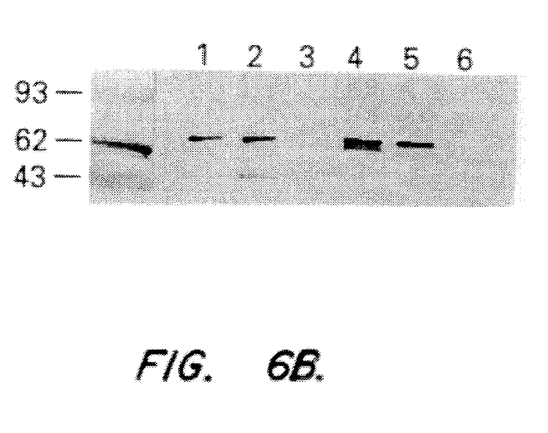

To confirm that these results were due to the reduction of MMP-2, conditioned media samples from experiments shown in FIG. 5 were concentrated 10-fold and electrophoresed. The samples were electrically transferred to membranes, and immunoblotted with specific polyclonal antibody to proMMP-2/TIMP-2 complex as described in Example 3. The results are shown in FIGS. 6A (HT1080) and 6B (A2058). Prestained molecular weight markers are shown to the left and lanes are as described above for FIG. 5. As for the gel zymograms above, FIGS. 6A and 6B show that compound 1 inhibits MMP-2 in a time-dependent manner and must be present during induction of MMP-2 by TGF-$\beta_1$ to inhibit its effects.

EXAMPLE 5

The Effect of Compound 1 on Transcription of MMP-2

This example illustrates the effect of compound 1 on MMP-1 and MMP-2 mRNA from A2058 cells using Northern blot analysis.

Total cytoplasmic RNA was purified from A2058 cells using cesium chloride density centrifugation. Cells were treated with DMSO vehicle (0.05 %) or compound 1 (2 μM) for 24 or 48 hr. Total RNA yields from treated and control cells (μg/$10^6$ cells) were similar. Aliquots (5 μg) of total RNA were denatured and separated on formaldehyde-1% agarose slab gels, passively transferred to GeneScreen, and crosslinked using ultraviolet light exposure. RNA was hybridized in buffer (50% deionized formamide, 5x SSC, 10 mM Tris HCl pH 7.5, 1x Denharts solution without albumin, 1.0% SDS, and 0.125 mg/mL salmon sperm DNA) containing $10^6$ counts/mL of $^{32}$P- labeled probe of either MMP-2, MMP-1, or with GAPDH which was used as a measure of RNA load. Probes were labeled to high specific activity with $^{32}$P-dCTP using a random primer labeling protocol. The cDNA probes for the MMP-2, MMP-1, and GAPDH have been described. See, Brown, et al., *Cancer Res.* 50:6184–6191 (1990); Templeton, et al., *Cancer Res.* 50:5431–5437 (1990); and Fort, et al., Nucleic Acids Res. 13:1431–1441 (1985). Radiolabeled bands were quantitated using laser densitometric analysis of autoradiography bands. Numeric data are presented as percent inhibition of IVase or interstitial collagenase expression corrected for loading using GAPDH.

Figure 7A:
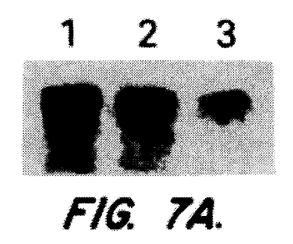

FIG. 7A shows transferred RNA which was hybridized with $^{32}$P-labeled cDNA for MMP-2. The RNA was prepared from A2058 cells incubated with 0.1% DMSO (lane 1), compound 1 for 24 hrs (lane 2) or compound 1 for 48 hrs (lane 3). A greater than 50% inhibition in MMP-2 transcription by treatment with compound 1 is demonstrated at 24 and 48 hr (corrected for loading). These data confirm that compound 1 inhibits collagenolytic function by inhibition of transcription of MMP-2.

Figure 7B:
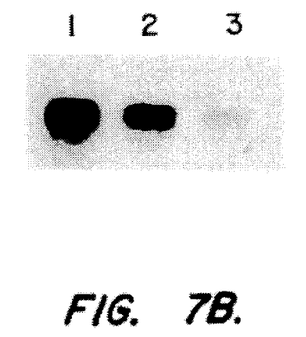

FIG. 7B shows similar results using $^{32}$P-labeled cDNA for MMP-1.

These results show that compound 1 inhibits the expression of interstitial collagenase MMP-1 and type IV collagenase/gelatinase A MMP-2.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of inhibiting expression of matrix metalloproteinase in a host afflicted with a disease associated with overexpression of matrix metalloproteinase, comprising treating said host with an effective amount of a compound of formula:

wherein:

is an integer of from 0 to 4;

Ar$^1$ and Ar$^2$ are each aromatic moieties independently selected from the group consisting of phenyl, naphthyl, and substituted versions thereof;

X is a linking moiety selected from the group consisting of O, S, SO$_2$, CO, CHCN, straight chain alkyl, alkoxy, and alkoxyalkyl; and Y is a nitrogen-containing heterocyclic moiety selected from the group consisting of: radicals of the formula wherein:

A is N or CH,

R$^1$ is a member selected from the group consisting of hydrogen,
—CONH$_2$, —CONHR$^5$, —CO$_2$H, —CO$_2$R$^5$, —SO$_2$NH$_2$, R$^2$ is a member selected from the group consisting of hydrogen, amino,
—NHCOC$_6$H$_5$, —NHCOR$^5$, —NHCHO, —NHR$^5$, —N(R$^5$)$_2$ and R$^5$ is lower alkyl of from 1 to 6 carbon atoms, and (b) 1,2,4-triazolyl, pyrazinyl, purinyl, pyrimidinyl, 1,2,3-triazolo-{4,5-d}-pyrimidinyl, and substituted versions thereof;

said disease being a member selected from the group consisting of nerve disorders, degenerative cartilagenous diseases, decubitus ulcers, arthritis, Alzheimer's disease, wound healing, corneal ulcers and fertility problems.

2. A method in accordance with claim 1 wherein Y is a radical of formula (II) and A is N.

3. A method in accordance with claim 1 wherein Y is a radical of formula (II), A is N, and R$^1$ is a member selected from the group consisting of hydrogen, —CONH$_2$, —CONHR$^5$, and —CO$_2$.

4. A method in accordance with claim 1 wherein Y is a radical of formula (II), A is N, and R$^1$ is —CONH$_2$.

5. A method in accordance with claim 1 wherein Y is a radical of formula (II), A is N, R$^1$ is —CONH$_2$, and R$^2$ is —NH$_2$.

6. A method in accordance with claim 1 wherein p is an integer of from 0 to 2, Ar$^1$ and Ar$^2$ are both substituted phenyl, X is a linking moiety selected from the group consisting of O, CO, and CHCN, Y is a radical of formula (II), R$^1$ is —CONH$_2$, and R$^2$ is —NH$_2$.

7. A method in accordance with claim 1 wherein p is 1, Ar$^1$ is 2,6-dichlorophenyl, Ar$^2$ is 4-chlorophenyl, X is CO, Y is a radical of formula (II), A is N, R$^1$ is —CONH$_2$, and R$^2$ is —NH$_2$.

8. A method in accordance with claim 1 wherein p is 1, Ar$^1$ is 2,6-dichlorophenyl, Ar$^2$ is 4-chlorophenyl, X is CO, Y is a radical of formula (II), A is N, R$^1$ is —CONH$_2$, and R$^2$ is —NHCHO.

9. A method in accordance with claim 1 wherein p is 1, Ar$^1$ is 2,6-dichlorophenyl, Ar$^2$ is 4-chlorophenyl, X is CO, Y is a radical of formula (II), A is N, R$^1$ is —CONH$_2$, and R$^2$ is —NHCOCH$_3$.

10. A method in accordance with claim 1 wherein p is 1, Ar$^1$ is 2,6-dichlorophenyl, Ar$^2$ is 4-chlorophenyl, X is CO, Y is a radical of formula (II), A is N, R$^1$ is —CONH$_2$, and R$^2$ is —NHCOC$_6$H$_5$.

11. A method in accordance with claim 1 wherein p is 1, Ar$^1$ is 2,6-dichlorophenyl, Ar$^1$ is 4-chlorophenyl, X is CO, Y is a radical of formula (II), A is N, R$^1$ is —CO$_2$H, and R$^2$ is —NH$_2$.

12. A method in accordance with claim 1 wherein said matrix metalloproteinase is MMP-2.

13. A method in accordance with claim 1 wherein said matrix metalloproteinase is MMP-1.

* * * * *